US012661476B2

(12) United States Patent (10) Patent No.: US 12,661,476 B2
Jagger et al. (45) Date of Patent: *Jun. 23, 2026

(54) CONTROL SYSTEM FOR PORTABLE OXYGEN CONCENTRATOR

(71) Applicant: 3B Medical, Inc., Dublin, OH (US)

(72) Inventors: Perry Karl Jagger, Hudson, WI (US); Theodore W. Jagger, White Bear Lake, MN (US); Albert A. Lucio, Haines City, FL (US)

(73) Assignee: 3B Medical, Inc., Winter Haven, FL (US)

( * ) Notice: Subject to any disclaimer, the term of this patent is extended or adjusted under 35 U.S.C. 154(b) by 29 days.

This patent is subject to a terminal disclaimer.

(21) Appl. No.: 18/539,372

(22) Filed: Dec. 14, 2023

(65) Prior Publication Data

US 2024/0123176 A1 Apr. 18, 2024

Related U.S. Application Data

(63) Continuation of application No. 16/989,950, filed on Aug. 11, 2020, now Pat. No. 11,878,120.

(51) Int. Cl.
*A61M 16/10* (2006.01)
*A61M 16/00* (2006.01)

(52) U.S. Cl.
CPC ........ *A61M 16/101* (2014.02); *A61M 16/022* (2017.08); *A61M 2016/0018* (2013.01);
(Continued)

(58) Field of Classification Search
CPC ...................................... A61M 16/0666–0672
See application file for complete search history.

(56) References Cited

U.S. PATENT DOCUMENTS 2,693,800 A 11/1954 Caldwell
3,529,594 A 9/1970 Charnley et al.
(Continued)

FOREIGN PATENT DOCUMENTS

WO WO-2020165761 A1 * 8/2020 ........ A61M 16/0003

OTHER PUBLICATIONS

3B Mask line up, 3B Medical, Youtube, [Posted on Mar. 26, 2019], [Site visited Aug. 20, 2021], Seen at URL: https://www.youtube. com/ watch?v=pf-rGz602WQ (Year: 2019).
(Continued)

*Primary Examiner* — Joseph D. Boecker
*Assistant Examiner* — Thomas W Greig
(74) *Attorney, Agent, or Firm* — Carlson, Gaskey & Olds. P.C.

(57) ABSTRACT

This disclosure relates to a control system for a portable oxygen concentrator (POC). Specifically, this disclosure relates to a method and a system configured for use with an oxygen delivery system that includes nasal fitting which does not include nostril prongs. Because the nasal fitting does not include nostril prongs, user comfort is dramatically increased relative to prior designs. That said, because the fitting is free of nostril prongs, changes in pressure associated with the user's breathing register less than in oxygen delivery systems with traditional fittings (i.e., those that include nostril prongs). As such, the method and system of this disclosure is configured to associate relatively small changes in pressure with a breathing cycle of a user, thereby permitting effective and efficient POC operation.

20 Claims, 6 Drawing Sheets

(52) U.S. Cl.
 CPC .............. *A61M 2016/0027* (2013.01); *A61M 2209/088* (2013.01)

(56) References Cited

U.S. PATENT DOCUMENTS

| | | | |
|---|---|---|---|
| 3,682,171 | A | 8/1972 | Dali et al. |
| 4,216,769 | A | 8/1980 | Grimes |
| 4,273,124 | A | 6/1981 | Zimmerman |
| 4,744,356 | A * | 5/1988 | Greenwood ...... A61M 16/0677 128/207.18 |
| 5,526,806 | A | 6/1996 | Sansoni |
| 5,527,806 | A * | 6/1996 | Holt ....................... C07J 73/005 546/77 |
| 5,928,189 | A | 7/1999 | Phillips et al. |
| 6,119,694 | A | 9/2000 | Correa et al. |
| 6,354,293 | B1 * | 3/2002 | Madison ........... A61M 16/1085 128/207.18 |
| 7,007,694 | B2 | 3/2006 | Aylsworth et al. |
| D549,323 | S | 8/2007 | Kwok et al. |
| 7,383,839 | B2 | 6/2008 | Porat et al. |
| D612,934 | S | 3/2010 | Prentice et al. |
| D626,646 | S | 11/2010 | Lubke et al. |
| D627,059 | S | 11/2010 | Wood et al. |
| D662,200 | S | 6/2012 | Eghbal et al. |
| 8,684,005 | B2 | 4/2014 | Jablons |
| D724,720 | S | 3/2015 | O'Connor et al. |
| 9,162,034 | B2 | 10/2015 | Veliss et al. |
| 9,180,270 | B2 | 11/2015 | Kapust et al. |
| D745,141 | S | 12/2015 | Hung |
| D752,735 | S | 3/2016 | Scampoli |
| D757,930 | S | 5/2016 | Baecke et al. |
| 9,393,375 | B2 | 7/2016 | Hernandez et al. |
| D768,287 | S | 10/2016 | Gusky et al. |
| 9,474,469 | B2 | 10/2016 | Deutsch et al. |
| D825,053 | S | 8/2018 | Ronayne et al. |
| 10,137,262 | B2 * | 11/2018 | Lee ................... A61M 16/0003 |
| 10,166,357 | B2 | 1/2019 | Veliss et al. |
| D848,605 | S | 5/2019 | Eury |
| D849,242 | S | 5/2019 | Wilson et al. |
| D849,243 | S | 5/2019 | Wilson et al. |
| D859,646 | S | 9/2019 | Scampoli et al. |
| D865,943 | S | 11/2019 | Wilson et al. |
| D878,549 | S | 3/2020 | Wilson et al. |
| D881,382 | S | 4/2020 | Chang |
| D893,013 | S | 8/2020 | Higgins et al. |
| D893,015 | S | 8/2020 | Wilson |
| D898,899 | S | 10/2020 | Rummery |
| 10,821,252 | B2 | 11/2020 | Chodkowshi |
| D911,515 | S | 2/2021 | Koschany et al. |
| D916,276 | S | 4/2021 | Wilson et al. |
| 10,987,480 | B1 | 4/2021 | Lucio |
| D933,206 | S | 10/2021 | Lucio |
| 11,266,803 | B2 | 3/2022 | Bell et al. |
| D973,197 | S | 12/2022 | Blanch et al. |
| D978,334 | S | 2/2023 | Kalnin |
| D978,335 | S | 2/2023 | Kalnin |
| 11,666,722 | B2 | 6/2023 | Lucio |
| 2002/0092527 | A1 | 7/2002 | Wood |
| 2003/0079749 | A1 | 5/2003 | Strickland et al. |
| 2003/0111081 | A1 | 6/2003 | Gupta |
| 2004/0226566 | A1 | 11/2004 | Gunaratnam et al. |
| 2005/0028822 | A1 | 2/2005 | Sleeper et al. |
| 2006/0107958 | A1 | 5/2006 | Sleeper |
| 2006/0266361 | A1 | 11/2006 | Hernandez |
| 2007/0095347 | A1 * | 5/2007 | Lampotang .......... A61B 5/0836 128/204.23 |
| 2007/0107737 | A1 | 5/2007 | Landis et al. |
| 2008/0060649 | A1 | 3/2008 | Veliss et al. |
| 2010/0113956 | A1 | 5/2010 | Curti et al. |
| 2010/0252042 | A1 | 10/2010 | Kapust et al. |
| 2010/0313898 | A1 | 12/2010 | Richard et al. |
| 2011/0073116 | A1 | 3/2011 | Genger et al. |
| 2011/0094518 | A1 * | 4/2011 | Cipollone ......... A61M 16/0683 128/207.18 |
| 2011/0214676 | A1 | 9/2011 | Allum et al. |
| 2012/0111332 | A1 | 5/2012 | Gusky et al. |
| 2012/0330118 | A1 | 12/2012 | Allum et al. |
| 2014/0094669 | A1 | 4/2014 | Jaffe et al. |
| 2015/0068928 | A1 | 3/2015 | Turner |
| 2016/0051787 | A1 | 2/2016 | Matsubara et al. |
| 2016/0095996 | A1 * | 4/2016 | Gusky ............... A61M 16/0816 128/205.25 |
| 2016/0166797 | A1 * | 6/2016 | Orr ................... A61M 16/0677 128/204.23 |
| 2016/0271353 | A1 | 9/2016 | Cheung et al. |
| 2016/0375215 | A1 | 12/2016 | Wilkinson et al. |
| 2017/0224942 | A1 | 8/2017 | Barbour et al. |
| 2019/0091428 | A1 * | 3/2019 | Chodkowski ..... A61M 16/0666 |
| 2019/0099570 | A1 | 4/2019 | Brambilla et al. |
| 2019/0240438 | A1 | 8/2019 | Stenzler et al. |
| 2020/0023153 | A1 | 1/2020 | Chou et al. |
| 2020/0281275 | A1 | 9/2020 | Jordan et al. |
| 2021/0338960 | A1 | 11/2021 | Schwaiger et al. |
| 2022/0126052 | A1 | 4/2022 | Fitch et al. |

OTHER PUBLICATIONS

Rio Replacement Nasal Pillow Cushion By 3B Medical,1800cpap. com,[Post date unknown], [Site visited Aug. 20, 2021], Seen at URL: https://www.1800cpap.com/rio-replacement-nasal-pillow-cushion-by-3b-medical?quantity=1&size=Large&gclid=EAlalQobChMI-9LC4um_8glVi4rlCh0a%2525E2%252580%2525A6 (Year: 2021).

3B Medical Introduces Oxygen Nasal Cannula, rtmagazine.com, Posted: 8/03/202 [online], site visited: [Mar. 3, 2023}, URL :<https://rtmagazine.com/products-treatment/monitoring-treatment/therapy-devices/3b-medical-freedom-x-nasal-cannula/>. (Year: 2020).

* cited by examiner

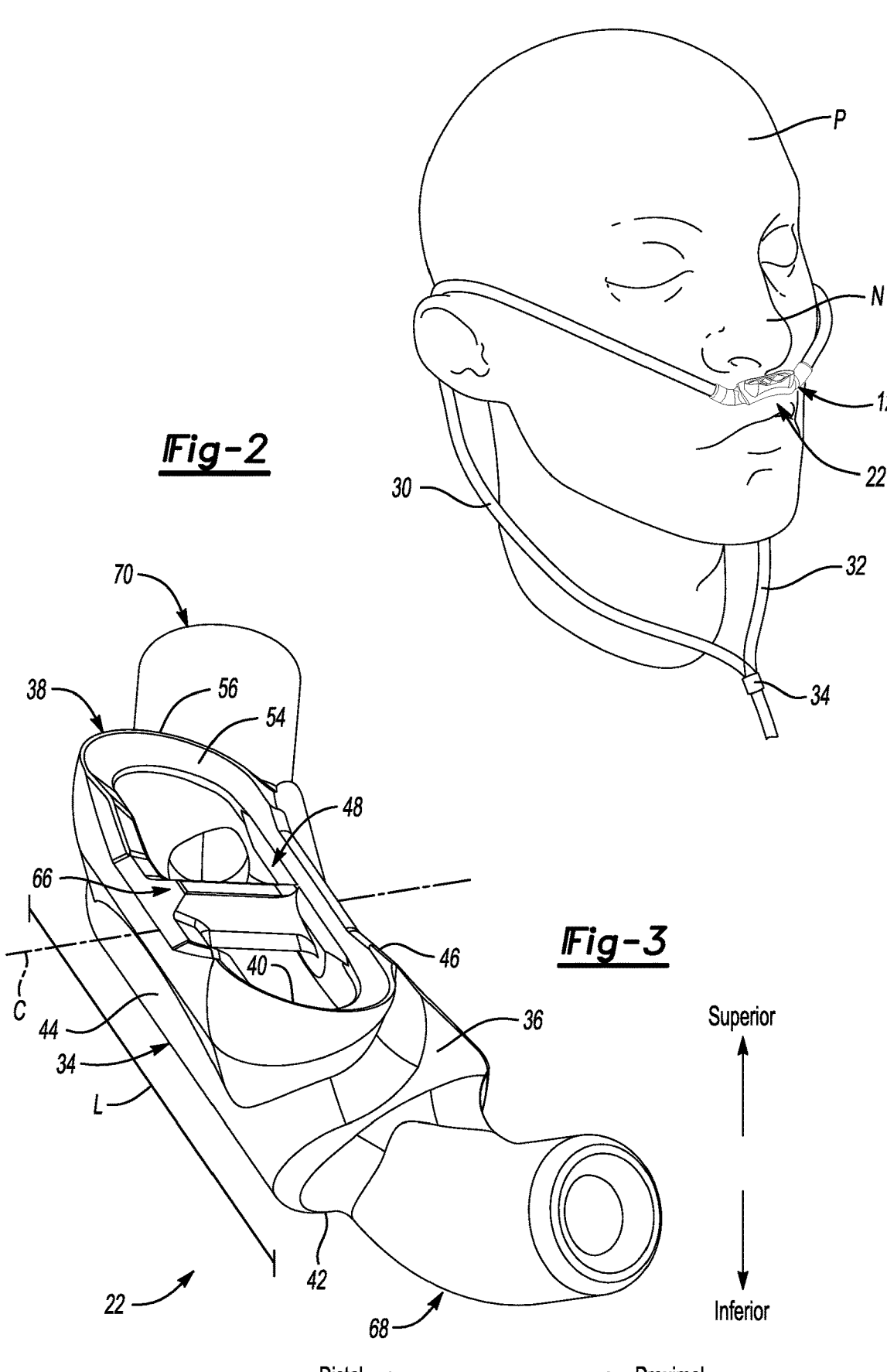
_Fig-2_
_Fig-3_
Superior
Inferior
Distal ⟵                    ⟶ Proximal Distal ◄──────      ──────► Proximal Distal ◄——————  ——————► Proximal

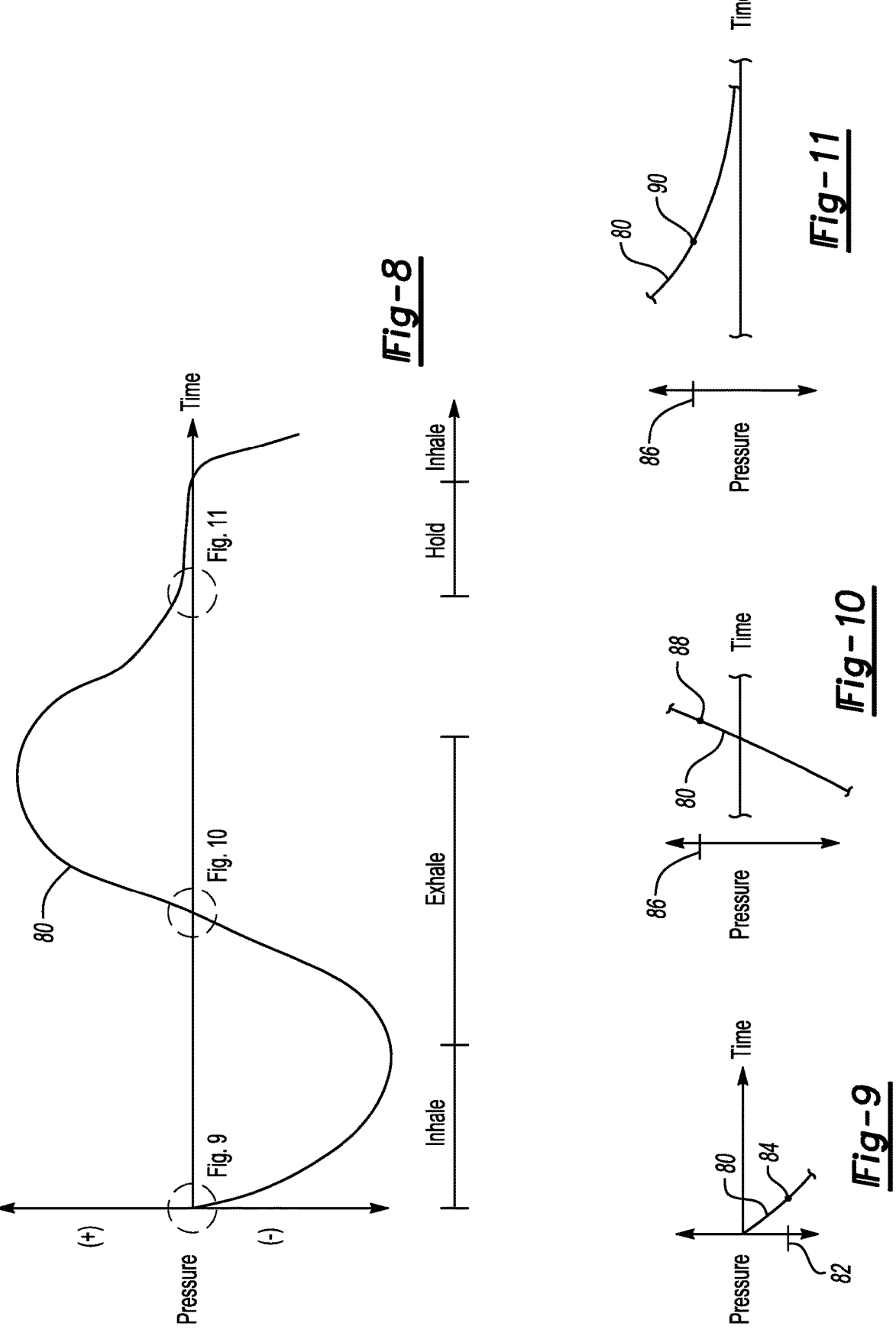

CONTROL SYSTEM FOR PORTABLE OXYGEN CONCENTRATOR

CROSS-REFERENCE TO RELATED APPLICATION

This application is a continuation of U.S. Non-Provisional patent application Ser. No. 16/989,950 filed on Aug. 11, 2020.

TECHNICAL FIELD

This disclosure relates to a control system for a portable oxygen concentrator (POC).

BACKGROUND

In the medical field, oxygen may be supplied to patients to treat a variety of conditions such as heart failure, chronic obstructive pulmonary disease (COPD), or any weakened lung or heart state. Portable oxygen concentrators (POCs) are one known device used in the medical field to supply supplemental oxygen to a patient. POCs take in ambient air, filter it, and deliver a relatively high purity flow of oxygen to the patient. At times, supplemental oxygen is used for purposes outside of the medical field, such as for recreational purposes. Supplemental oxygen may be used to shorten recovery time for exhausted athletes, or may be used at high altitudes to make breathing easier during skiing, mountain biking, or other sporting activities.

SUMMARY

A method according to an exemplary aspect of the present disclosure includes, among other things, detecting an inhale of a user when a difference between a pressure reading and a baseline value is less than or equal to an inhale threshold. The baseline value is based on preceding breaths of the user. Further, the user is breathing relative to a fitting of a nasal cannula of an oxygen delivery system, which includes a tube connecting the fitting to an oxygen supply. The fitting is situated inferior to the nostrils of the user and does not include nostril prongs. The method further includes the step of delivering oxygen to the user via the fitting in response to the detected inhale.

In a further embodiment, the inhale threshold is within a range of −0.01 to −0.04 in $H_2O$.

In a further embodiment, the inhale is detected when a predetermined amount of successive pressure readings, as compared to the baseline value, are less than or equal to the inhale threshold.

In a further embodiment, the predetermined amount of successive pressure readings is within a range of 4 to 32 pressure readings.

In a further embodiment, the method includes detecting an exhale of the user when a difference between a pressure reading and the baseline value is greater than or equal to an exhale threshold.

In a further embodiment, the exhale threshold is within a range of 0.01 to 0.04 in $H_2O$.

In a further embodiment, the exhale is detected when a predetermined amount of successive pressure readings, as compared to the baseline value, are greater than or equal to the exhale threshold.

In a further embodiment, the predetermined amount of successive pressure readings is within a range of 4 to 32 pressure readings.

In a further embodiment, the step of detecting includes analyzing a signal from a pressure sensor of the oxygen delivery system.

In a further embodiment, the pressure sensor is a differential pressure sensor with a first port in fluid communication with the tube and a second port arranged such that the second port is isolated from environmental conditions.

In a further embodiment, the oxygen supply is a portable oxygen concentrator.

In a further embodiment, the delivering step includes delivering a pulse of oxygen to the user via the fitting.

An oxygen delivery system according to an exemplary aspect of the present disclosure includes among other things, an oxygen supply, a tube configured to connect to the oxygen supply, a fitting configured to connect to the tube and configured to be situated inferior to a nose of a user. The fitting does not include nostril prongs. The system further includes a pressure sensor configured to generate signals indicative of pressure in the tube, and a controller configured to read the signals from the pressure sensor. The controller is configured detect an inhale of a user when a difference between a pressure reading and a baseline value is less than or equal to an inhale threshold, and the baseline value is based on preceding breaths of the user.

In a further embodiment, the controller is configured to detect an exhale of the user when a difference between a pressure reading and the baseline value is greater than or equal to an exhale threshold, and, after detecting the exhale and before detecting a subsequent inhale, detect a pause in a breathing cycle of the user when a difference between the pressure reading and the baseline value is less than or equal to the exhale threshold.

In a further embodiment, the controller is configured to take a predetermined amount of pressure readings during the pause in the breathing cycle.

In a further embodiment, the inhale threshold is within a range of −0.01 to −0.04 in $H_2O$ and the exhale threshold is within a range of 0.01 to 0.04 in $H_2O$.

BRIEF DESCRIPTION OF THE DRAWINGS

FIG. 2 is a close-up view of a portion of an example cannula relative to a head and neck of a patient.

FIG. 3 is a front-perspective view of an example fitting of the example cannula.

FIG. 8 is a graphical representation of changes in pressure relative to time during an example breathing cycle.

FIG. 9 is a close-up view of the corresponding encircled area in FIG. 8.

FIG. 10 is a close-up view of the corresponding encircled area in FIG. 8.

FIG. 11 is a close-up view of the corresponding encircled area in FIG. 8.

DETAILED DESCRIPTION

This disclosure relates to a control system for a portable oxygen concentrator (POC). Specifically, this disclosure relates to a method and a system configured for use with an oxygen delivery system that includes nasal fitting which does not include nostril prongs. Because the nasal fitting does not include nostril prongs, user comfort is dramatically increased relative to prior designs. That said, because the fitting is free of nostril prongs, changes in pressure associated with the user's breathing register less than in oxygen delivery systems with traditional fittings (i.e., those that include nostril prongs). As such, the method and system of this disclosure is configured to associate relatively small changes in pressure with a breathing cycle of a user, thereby permitting effective and efficient POC operation. These and other benefits will be appreciated from the below description.

Figure 1:
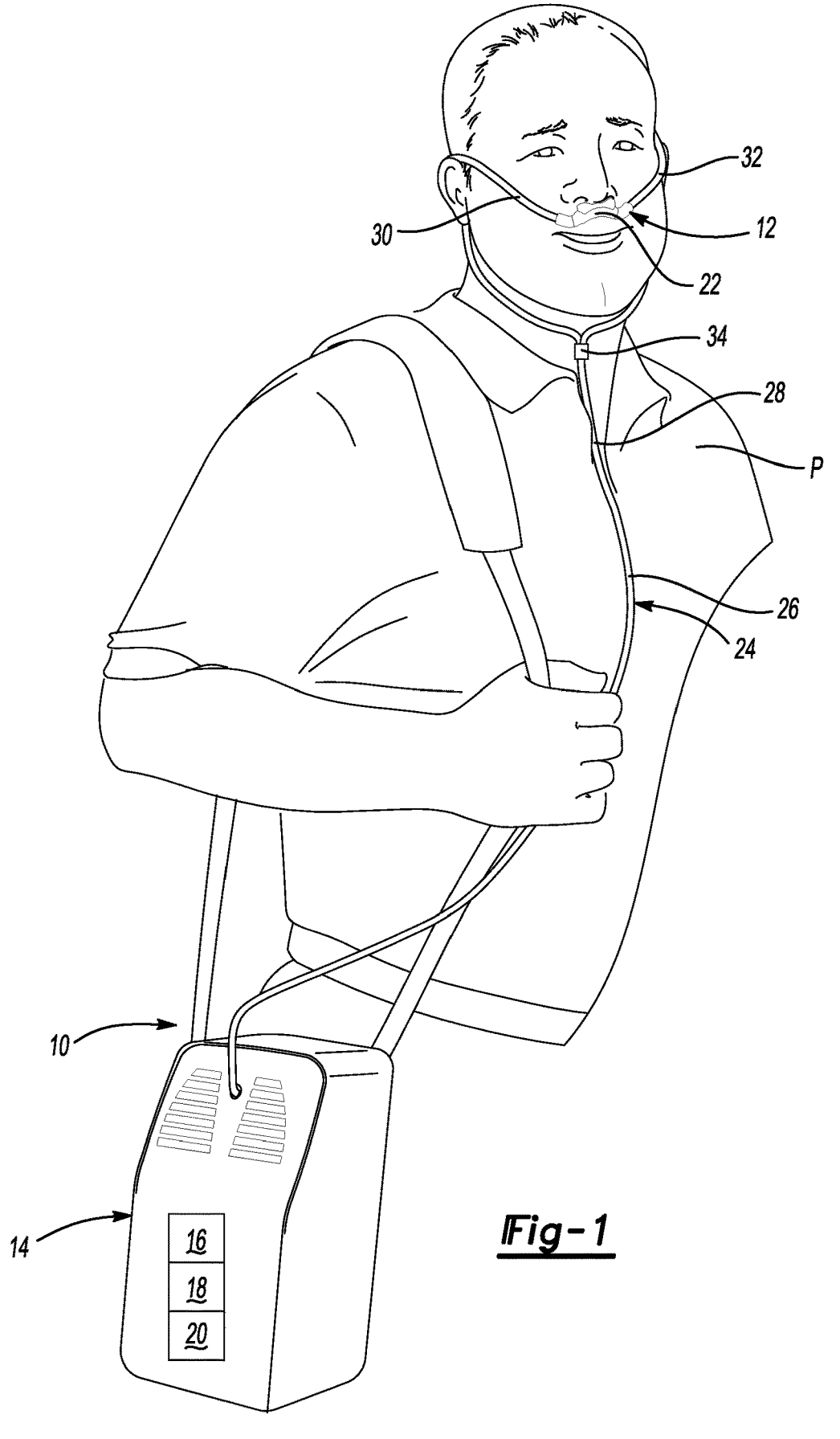
FIG. 1 illustrates, somewhat schematically, an example oxygen delivery system.
Figure 4:
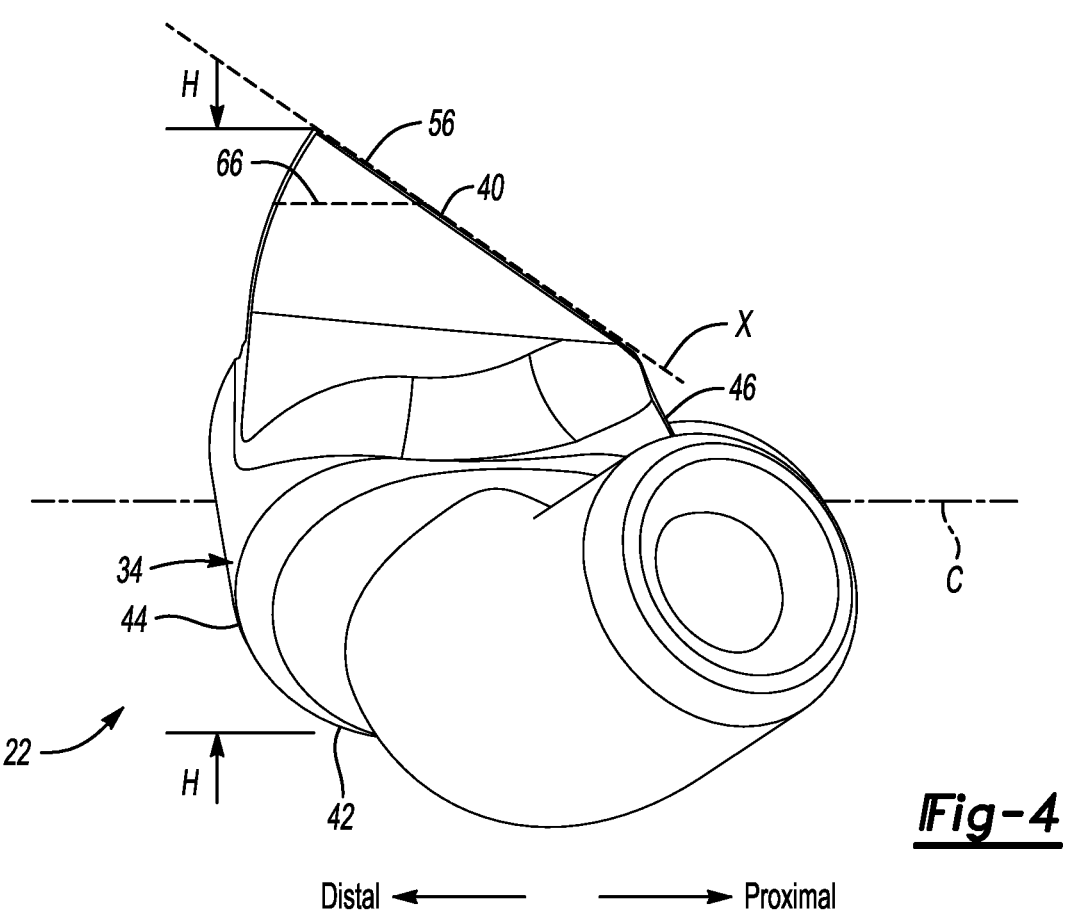
FIG. 4 is a side of view of the example fitting.

FIG. 1 illustrates an example oxygen delivery system 10 ("system 10") with a cannula 12 and an oxygen supply 14. The cannula 12 may be considered a cannula assembly, as it may contain more than one piece, such as a tube and a nasal fitting, among other pieces (such as connectors and collars) as explained below. The oxygen supply 14 is configured to deliver a flow of supplemental oxygen or increased airflow to a patient, user, or person, P, who is typically a person in need of respiratory help. Alternatively, the patient P could be a person who does not require oxygen for medical purposes but, on the contrary, is an athlete using oxygen for recovery purposes. Further, the patient P could be an athlete engaging in extreme sports, such as skiing or mountain biking, and in particular the patient P could be engaging in such sports at substantially high altitudes, such as in mountainous regions. Thus, the term patient P is used herein to refer to any user of the system 10 and is not intended to refer to those who require the system for medical purposes.

In FIG. 1, the oxygen supply 14 is a portable oxygen concentrator (POC). It should be understood that this disclosure extends to cannulas used with other types of oxygen supplies, including oxygen tanks, stationary oxygen concentrators, or a wall connection in a hospital via a flowmeter. This disclosure also extends to cannulas used with other breathing aids, such as a continuous positive airway pressure (CPAP) machine.

The oxygen supply 14 includes an blower 16, such as a pump and/or an air compressor, a sensor 18, and a controller 20, among other structures and components, such as one or more filters, such as a molecular sieve which separates (i.e., adsorbs) nitrogen from ambient air, and a battery. The blower 16, sensor 18, and controller 20 are shown schematically in FIG. 1. The oxygen supply 14 may use pressure swing adsorption (PSA), vacuum swing adsorption (VSA), or pressure vacuum swing adsorption (PVSA) technology. The oxygen supply 14 may further include a storage chamber, or reservoir. The battery of the oxygen supply 14 may be rechargeable.

The oxygen supply 14 delivers oxygen via the cannula 12 to an interface, which in this example is provided by a nasal fitting 22 ("fitting 22"). The fitting 22 rests beneath a nose of the patient P and delivers oxygen to patient P via their nose N (FIG. 2). The oxygen supply 14 may be a pulse delivery device or a continuous flow device. A continuous flow POC provides a continuous flow of oxygen to the patient. A pulse delivery POC only provides oxygen when the patient P is inhaling. The sensor 18 is configured to generate information (i.e., a signal) indicative of when the patient P is inhaling by detecting a change in pressure. In this sense, the sensor 18 may be considered a pressure sensor. The controller 20 is configured to interpret the signal from the sensor 18 and, when a particular change in pressure is identified, the controller 20 instructs the blower 16 to deliver a pulse of oxygen to the patient P. As will be discussed below, the sensor 18 is relatively sensitive compared to traditional sensors, and the controller 20 is configured to instruct the blower 16 to provide a pulse of oxygen when a relatively low change in pressure is met or exceeded.

Ambient air contains about 21% oxygen and about 79% nitrogen and other gases. The oxygen supply 14 compresses the ambient air and filters the nitrogen out of the air, leaving oxygen as the primary gas in the product fluid flow delivered to the user via the fitting 22. The nitrogen is released back to the ambient environment and/or held in the filters. In a typical medical grade POC, the gas delivered to the patient P is around 90-95% oxygen. In other embodiments, such as in POCs for recreational use, a lower oxygen purity is delivered to the patient P. The oxygen supply 14 may include flow control buttons and indicators for breath detection or alerts, and sometimes includes the ability to toggle between a continuous flow and a pulse flow.

The controller 20 may include hardware and/or software, and may be programmed with executable instructions for interfacing with and operating the various components of the oxygen supply 14. In an embodiment, the controller 20 and the sensor 18 are mounted to a common printed circuit board within the oxygen supply 14. It should be understood that the controller 20 could be part of an overall control module. The controller 20 includes a processing unit and non-transitory memory for executing the various control strategies and modes of the oxygen system 14.

In this example, the cannula 12 includes a tube 24 fluidly connecting the oxygen supply 14 to the fitting 22. The tube 24, in this example, includes a main section 26 connected directly to the oxygen supply 14 and extending to a split 28. At the split 28, the tube 24 branches into a first portion 30 and a second portion 32, each of which are connected directly to a respective side of the fitting 22. The first and second portions 30, 32 wrap around opposite ears of the patient P. An adjustable collar 34, which is slidable along the first and second portions 30, 32, is below a chin of the patient P.

The fitting 22 rests below a nose N of the patient, as shown in FIG. 2. In particular, the fitting 22 rests against the face of the patient P, specifically against the philtrum, including the philtral dimple and/or the philtral columns, at a location superior to (e.g., vertically above) the upper lip and inferior to (e.g., vertically below) the base of the nose N.

The fitting 22 does not include nostril prongs, which are found in traditional nasal cannulas and CPAP nasal pillows. Nostril prongs are structures, namely protrusions, which enter into the nostrils of the patient P. In this disclosure, the fitting 22 does not include any such structures that project into the nostrils of the patient P. In fact, in some examples, the fitting 22 is spaced-apart from the nose N of the patient P, and rests against an area superior to the upper lip of the patient P without directly contacting the nose N. In other examples, the columella (i.e., the inferior margin of the septum) of the nose N may contact a superior (i.e., upper) surface of the fitting 22. In either example, no portion of the fitting 22 enters the nostrils of the patient P. Further, in this disclosure, the fitting 22 does not surround the tip of the nose, as is common in some known CPAP masks and CPAP pillows.

FIGS. 3-6 illustrate additional detail of the fitting 22. With joint reference to those figures, the fitting 22 is substantially symmetrical about its centerline C. Specifically, the fitting 22 is symmetrical about a plane containing the centerline C and extending in the superior and inferior directions, labeled in some figures for reference. The fitting 22 includes a main body portion 34 having a length L extending between a first lateral side 36 and a second lateral side 38 of the main body portion 34. In an example, the length L is about 22 mm. The term lateral refers to the lateral direction, which is substantially normal to the centerline C and the inferior and superior directions.

The main body portion 34 also includes a height H (FIG. 4) vertically between a superior (i.e., vertically upper) surface 40 and an inferior (i.e., vertically lower) surface 42. In one example, a ratio between a length L and the height H is about 2.2:1. The height H is 10 mm in an example. The main body portion 34 further includes a width W (FIG. 5) in a direction parallel to the centerline C between a distal (i.e., forward facing) surface 44 and a proximal (i.e., rearward facing) surface 46. A ratio between a length L and the width W is 2.2:1 The width W is 10 mm in an example. The ratio between the width W and height H is 1:1 in an example.

The superior surface 40 includes a single discharge port 48 in this example. In other words, the superior surface 40, and the fitting 22 overall, does not include more than one discharge port 48. Rather, in the embodiment of FIGS. 3-6, the fitting 22 includes a single discharge port 48 having a divider which divides the discharge port 48 into two sections, and in FIG. 7 the fitting 22 includes a single discharge port without a divider. Providing a single discharge port 48, which is larger by area than a nostril prong, for example, makes it easier for the fitting 22 to deliver flow to the nose N of the patient P and to collect exhaled flow from the nose N.

The discharge port 48 is configured to deliver fluid to the nose N of the patient P. In this example, the discharge port 48 is formed in the superior surface 40 of the main body portion 34. The discharge port 48 includes a first section 50 configured to be situated inferior to a first nostril of the patient P, and a second section 52 configured to be situated inferior to a second nostril of the patient P. The discharge port 48 is substantially stadium-shaped when viewed from above. Other shapes come within the scope of this disclosure, however.

An inclined wall 54 is provided adjacent the discharge port 48. The inclined wall 54 projects toward the center of the discharge port 48 and in the inferior direction from an apex 56 defining a superior-most portion of the fitting 22. The apex 56 circumscribes substantially the entire discharge port 48 and lies in a plane X. The plane X is inclined at approximately a 45° angle relative to the distal and proximal directions. The plane X also defines the superior boundary of the discharge port 48. The inclined wall 54 is inclined at an acute, and substantially constant, angle in the inferior direction relative to the plane X about its entire perimeter.

The inclined wall 54 assists in directing exhaled flow from the nostrils of the patient P back into the fitting 22. As such, the inclined wall 54 increases the ease of detecting exhalation, which is particularly relevant in the context of a pulse delivery device. Pulse delivery devices attempt to deliver a pulse of oxygen timed with a patient's inhalation. In an example, the controller 20 uses exhalation to time delivery of the next pulse of oxygen. In particular, when exhalation is detected, the controller 20 instructs the disclosed device to begin readying a pulse of oxygen for the patient's next inhalation. Since the fitting 22 does not include nasal prongs, it can in some circumstances be difficult to capture the airflow from the patient's exhalation. In turn, in those circumstances, it can be difficult to identify when exhalation occurs. The inclined wall 54 ensures that an adequate amount of exhalation airflow is captured, which makes it more likely that the sensor 18 and controller 20 will be able to identify the exhalation and, in turn, that the pulse device will function properly.

The fitting 22 includes a divider 58 located along the centerline C. The divider 58 is spaced inferior to the apex 56. In particular, the divider 58 is spaced inferior to the plane X. The divider 58 separates the first section 50 and the second section 52. The divider 58 is configured to deliver flow to and from the nostrils of the patient P. The divider 58, in this example, includes a central portion 60 providing a superior-most portion of the divider 58, a first wall 62 projecting from the central portion 60 toward the center of the first section 50 and in an inferior direction, and a second wall 64 projecting from the central portion 60 toward the center of the second section 52 and in the inferior direction. The first and second walls 62, 64 blend into the inclined wall 54 in this example. The first and second walls 62, 64 are inclined at the same angle relative to the plane X as the inclined wall 54 in this example. While a divider 58 is present in this embodiment, in other embodiments there is no divider and the first and second sections 52, 54 directly blend into one another, as in FIG. 7. When the divider 58 is present, the dimensions of the divider 58 can be adjusted. In particular, the central portion 60 can have a width of about 5-6 mm to correspond to a width of an average septum and/or columella.

Figure 5:
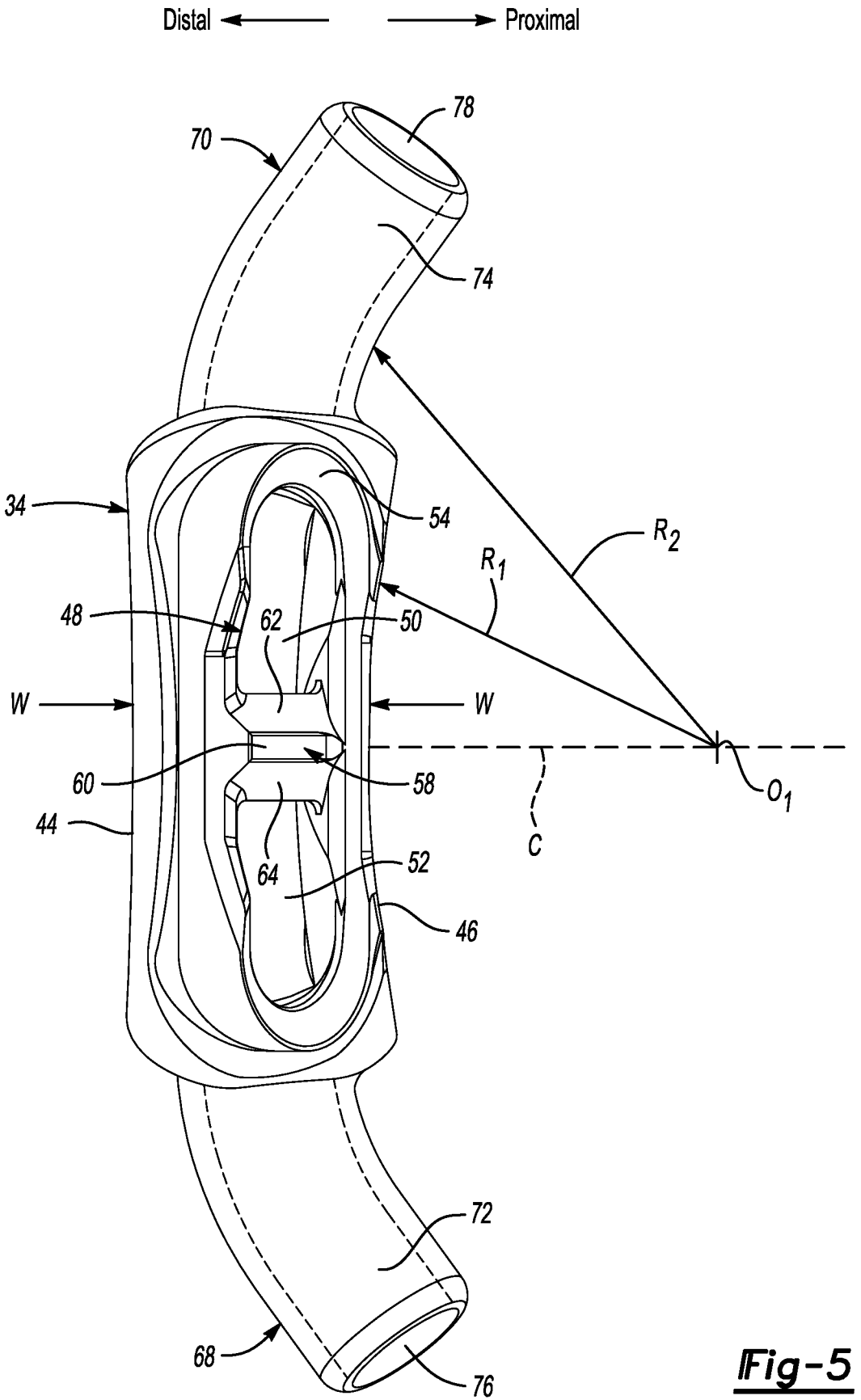
FIG. 5 is a top view of the example fitting.
Figure 6:
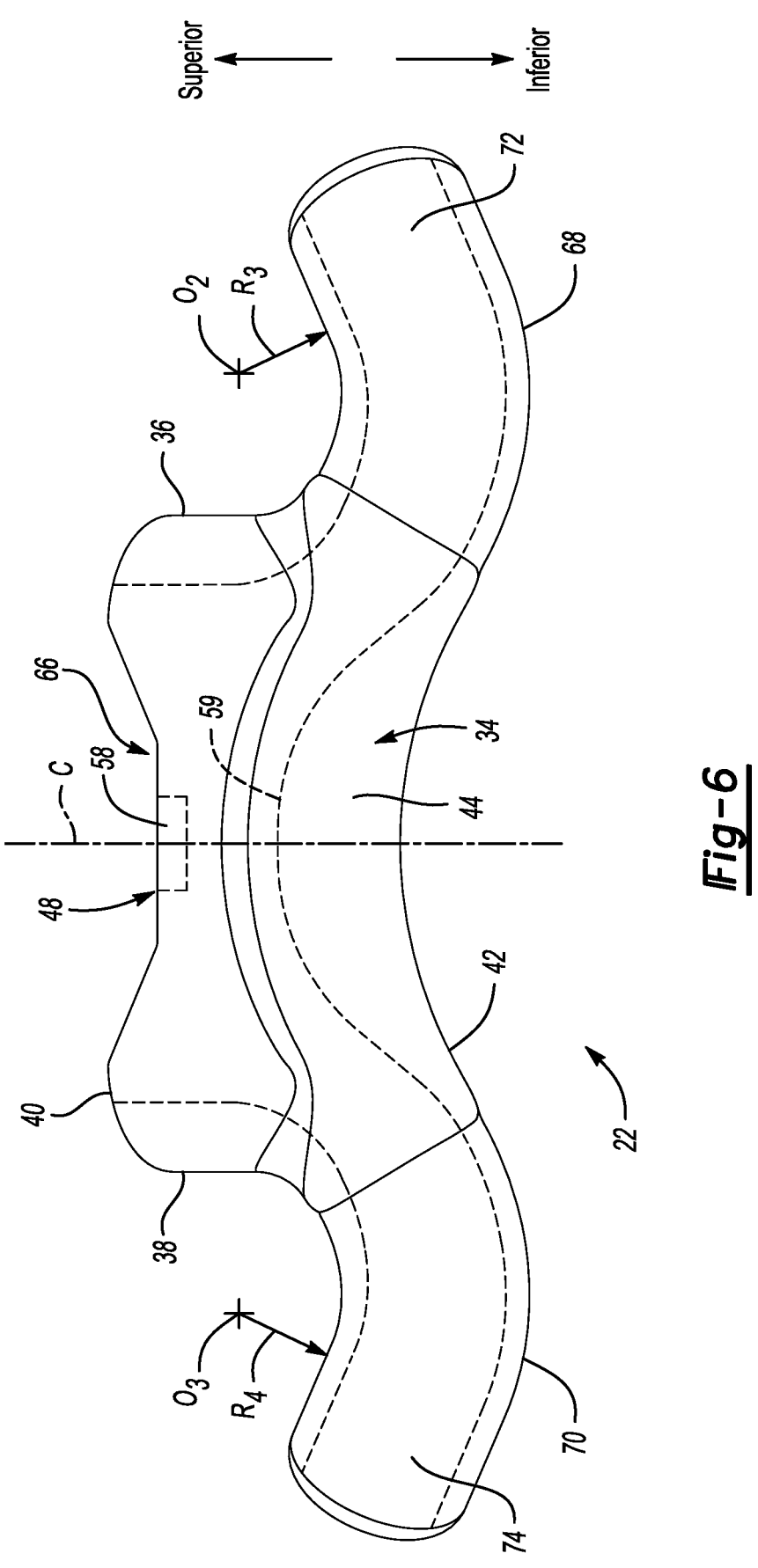
FIG. 6 is a front view of the example fitting.

With reference to FIG. 6, the inferior surface of the divider 58, in this example, is spaced-apart in a superior direction from a bottom wall 59 of an internal passageway of the fitting 22. The internal passageway(s) of the fitting 22 is represented in dashed lines in FIGS. 5 and 6. Fluid flowing to and from the first and second sections 50, 52 of the discharge port 48 can intermix in the space inferior to the divider 58 and superior to the bottom wall 59. The bottom wall 59 is convex when viewed from a superior location, and the apex of the bottom wall 59 is located on the centerline C. The curvature of the bottom wall 59 is configured to direct fluid to and from the internal passageways in the prongs located on the lateral sides of the main body portion 34 of the fitting 22, which will be discussed below. While the divider 58 assists with directing flow, in the example where there is no divider, the bottom wall 59 is used to direct fluid to and from the prongs.

Figure 7:
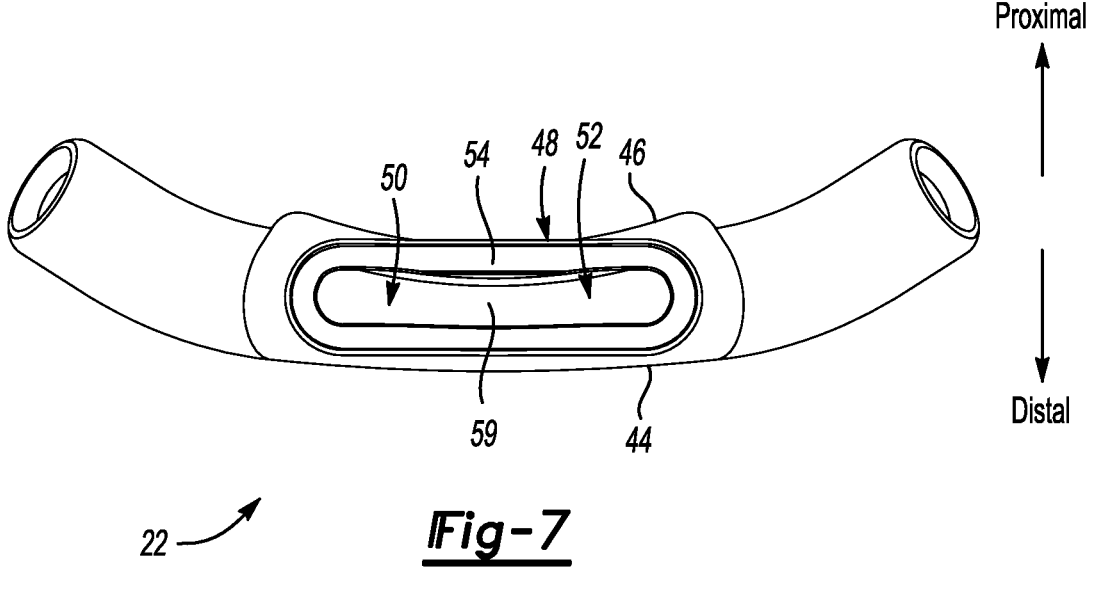
FIG. 7 is a top view of another example fitting.

The inclined wall 54 includes a notch 66 to accommodate a columella and/or tip of the nose N of the patient P. The notch 66 is formed in a distal-most portion of the inclined wall 54. The notch 66 is represented by dashed lines in FIG. 4. Because of the slope of the plane X, the notch 66 may increase comfort in some examples. The notch 66 is not present in all examples. In FIG. 7, for example, the inclined wall 54 continuously extends about its entire perimeter and does not include a notch. When the notch 66 is present, the notch 66 may be sized to correspond to a width of an average septum, columella, and/or tip of the nose.

Various aspects of this disclosure relate to preventing undesired movement of the fitting 22 relative to the nose N of the patient P during use. The nasal prongs of traditional cannulas typically resist such movement. Because the fitting 22 does not include nasal prongs, the fitting 22 includes other various features which resist movement. In one aspect of this disclosure, the proximal surface 46 of the main body portion 34 is curved. Specifically, as shown in FIG. 5, the proximal surface 46 is concave when viewed from the proximal direction. More particularly, the proximal surface 46 exhibits a contour following a constant radius $R_1$ having an origin $O_1$, which is on the centerline C and is spaced-apart from the main body portion 34 in the proximal direction. The contour of the proximal surface 46 corresponds to the contour of the philtrum of the patient P.

The fitting 22 also includes first and second prongs 68, 70 projecting laterally from the first and second sides 36, 38 of the main body portion 34, respectively. The first and second prongs 68, 70 are configured to couple to respective ends of the tube 24. The first and second prongs 68, 70 are sized and shaped to resist movement of the fitting 22 during use, as will be discussed below.

In general, the first and second prongs 68, 70 include respective bores, each providing a respective internal passageway 72, 74 which ultimately leads to the discharge port 48 and is represented by dashed lines in FIG. 5. The internal passageways 72, 74 follow the contour of the first and second prongs 68, 70. The first and second prongs 68, 70 includes respective inlet ports 76, 78 leading into the respective internal passageways 72, 74. The internal passageways 72, 74 meet at a location inferior to the discharge port 48 and, when present, the divider 58.

When viewed from a top (i.e., superior) perspective, as in FIG. 5, the first and second prongs 68, 70 exhibit a curvature. Specifically, the first and second prongs 68, 70 are concave when viewed from the proximal direction. A proximal surface of the first and second prongs 68, 70 follows a constant radius $R_2$ having the origin $O_1$. The radius $R_2$ is larger than the radius $R_1$ in this example such that the prongs 68, 70 fit relative to the patient P in a manner which corresponds to the upper lip of the patient P on the lateral sides of the philtrum.

The first and second prongs 68, 70 also exhibit a curvature when viewed from another perspective. With reference to FIG. 6, the first and second prongs 68, 70 are concave when viewed from a superior location. Specifically, the first prong 68 is curved such that a superior surface of the first prong 68 follows a radius $R_3$ having an origin $O_2$ superior to the first prong 68 and spaced laterally from the first side 36 of the main body portion 34. Further, the second prong 70 is curved such that a superior surface of the second prong 70 follows a radius $R_4$ having an origin $O_3$ superior to the second prong 70 and on the second side 38 of the main body portion 34. The radii $R_3$, $R_4$ are the same in this example.

The first and second prongs 68, 70 are symmetrical about the centerline C. The first and second prongs 68, 70 are substantially cylindrically-shaped in cross-section such that all sides of the first and second prongs 68, 70 (i.e., not just the above-mentioned proximal and superior surfaces), and the internal passageways 72, 74, are curved according to the above-discussed curvatures.

The above-discussed orientation of the first and second prongs 68, 70 resists undesired movement of the fitting 22. In particular, the above-discussed orientation resists the tendency of the fitting 22 to flip forward, in the distal direction, as the upper lip moves during speech. Thus, the orientation keeps the discharge port 48 oriented toward the nostrils of the patient P. In part, the resistance to flipping forward is brought about by the inlet ports 76, 78 being located inferior to, or below, the discharge port 48, and namely the plane X. In this way, the tension on the fitting brought about by the tube 24, and countered by the nose N of the patient P, tends to maintain the position of the fitting 22. Specifically, the position of the fitting 22 is more stable and is not easily altered during speech or other activities.

When worn by the patient, the discharge port 48 is configured to be situated inferior to (i.e., vertically beneath) the nose N of the patient P, and specifically such that the first section 50 is inferior to a right nostril (from the patient's perspective) of the patient P and the second section 52 is configured to be situated inferior to a left nostril of the patient P. Further, the divider 58 and notch 66 are configured to be situated inferior to a columella and/or tip of the nose N of the patient P.

The fitting 22 is integrally formed as a one-piece structure in one example. In particular, the fitting 22 is provided by an integrally molded piece of plastic. In some embodiments, the fitting 22 is made entirely of silicone, or another soft elastomer. The fitting 22 may be made of same material as tube 24 or a different material. While above the fitting 22 was described as being separate from the tube 24, the fitting 22 could be formed integrally with the tube 24.

Because the fitting 22 does not include nostril prongs and no portion of the fitting 22 enters the nostrils of the patient P, patient comfort is dramatically increased relative to traditional nasal cannula and nasal pillow designs. However, because the discharge port of the fitting 22 is further away from the nostrils of the patient P than in cannulas with nostril prongs, for example, various operating parameters and settings of the system 10 are adjusted in this disclosure relative to previous, known oxygen delivery systems.

Another aspect of this disclosure relates to a control system for the system 10. The control system includes the components of the system 10. In this aspect of the disclosure, the controller 20 is programmed in a particular manner such that the system 10 performs effectively and efficiently despite the challenges associated with a fitting 22 that does not include nostril prongs. While specific fittings without nostril prongs are shown in FIGS. 1-7, this disclosure extends to other types of fittings that do not include nostril prongs. This disclosure could also be used relative to fittings that do include nostril prongs, but has particular benefits in fittings without nostril prongs. Further, this disclosure has particular benefits when used with portable oxygen concentrators (POCs) but could be used with other devices.

Because the fitting 22 does not have nostril prongs, the signal from the sensor 18 in response to a breathing cycle of a user registers substantially less than if the fitting 22 had nostril prongs. Thus, the controller 20 is programmed to identify various aspects of a breathing cycle, such as an inhale (inspiration) and exhale (expiration), at relatively low pressures that would not be associated with an inhale or exhale, for example, in traditional systems including nasal fittings with nostril prongs. An example control strategy will now be described.

FIG. 8 is a graphical representation of a breathing cycle, illustrated relative to a plot of pressure versus time, with pressure on the Y-axis and time on the X-axis. FIGS. 9-11 are close-up views of various portions of FIG. 8. As the user inhales and exhales, the pressure reading of the sensor 18 changes. The controller 20 is configured to interpret, or read, the signal from the sensor 18 and to issue instructions or commands to various aspects of the system 10 in response to those signals.

With reference to FIGS. 8-11, a line 80 is representative of the output of the sensor 18 during an example, normal breathing cycle of a user. Beginning at time zero, the user begins a breathing cycle by inhaling and the line 80 gradually moves downward, indicating a pressure drop. In this example, the controller 20 will identify an inhale of the user when a difference between a pressure reading and a baseline value, or zero value, is less than or equal to an inhale threshold 82. The baseline value is determined based on preceding breaths of the user. In FIGS. 8-11, the baseline value is represented by the X-axis. The baseline value can be adjusted over time, as will be explained.

In this example, the inhale threshold 82 is within a range of −0.01 to −0.04 in $H_2O$. This is an order of magnitude lower than what would be associated with the onset of an inhale in traditional, known systems. In such prior systems, changes in pressure on the order of −0.01 in $H_2O$ would be disregarded as system noise or a mild variation in ambient conditions, such as a light breeze. In the present system, however, such minor pressure changes are associated with an inhale.

The present system is able to identify an inhale at such small pressure changes by routinely updating and adjusting the baseline value. The baseline value accounts for system noise and ambient conditions. The manner in which the baseline value is determined will be discussed below.

In order to avoid falsely identifying an inhale, the system does not identify an inhale until a predetermined amount of successive pressure readings, as compared to the baseline value, are less than or equal to the inhale threshold 82. In other words, the pressure reading minus the baseline value must be less than or equal to the inhale threshold 82. In a particular example, the pressure sensor 18 will provide a pressure reading at fixed time intervals, such as every 6 milliseconds, and the controller 20 will not identify an inhale until 10 successive pressure readings are equal to or below −0.01 in $H_2O$. While 10 pressure readings is mentioned as an example, in other examples the controller looks for a number of successive pressure readings between 4 and 32. In FIG. 9, the inhale threshold 82 is first reached at point 84, and the controller 20 identifies an inhale 60 milliseconds (10 readings 6 milliseconds apart) after point 84. Once the inhale is detected, the controller 20 issues instructions to deliver a pulse dose of oxygen to the user via the fitting 22.

After a period of time, the controller 20 identifies an exhale. The controller 20, in this example, identifies an exhale when a difference between a pressure reading and the baseline value is greater than or equal to an exhale threshold 86. In this example, the exhale threshold is within a range of 0.01 to 0.04 in $H_2O$. In order to avoid false indications of an exhale, the exhale is detected when a predetermined amount, such an amount within a range of 4 to 32 (such as 10), of successive pressure readings, as compared to the baseline value, are greater than or equal to the exhale threshold. In FIG. 10, the exhale threshold 86 is first reached at point 88, and the controller 20 identifies an exhale 60 milliseconds after point 88. The controller 20 issues instructions to cease delivery of oxygen during the exhale period.

After detecting the exhale and before detecting a subsequent inhale, the controller 20 monitors the reading of the sensor 18 and uses that information, in part, to determine the baseline value. Specifically, the controller 20 is programmed to detect a pause, labeled as "hold" in FIG. 8, in a breathing cycle. The pause is a time where the user is not inhaling or exhaling, and occurs during most if not all normal breathing cycles in healthy individuals. The pause is identified, relative to FIG. 11, when the line 80 falls back below the exhale threshold 86. Specifically, the pause is identified when a difference between the pressure reading and the baseline value is equal to or less than the exhale threshold 86. In FIG. 11, the controller 20 takes a taking a predetermined amount of pressure readings beginning at point 90, which is the first time the line 80 meets or falls below the exhale threshold 86 after an exhale is first identified. In an example, the controller 20 takes 16 readings, each 6 milliseconds apart. This 96 millisecond period begins at point 90 and finishes before the next breathing cycle begins (i.e., before the next inhale occurs), and thus each of the readings is above the baseline value in this example.

Because a user is not breathing during the pause in the breathing cycle, the pressure readings that occur during the aforementioned period are associated with changes in pressure attributable to noise in the system and/or ambient conditions. For instance, a blower configured to cool a printed circuit board of the system 14 could cause the sensor 18 to output a positive pressure signal during this period. Alternatively or in addition, wind entering the fitting 22 could cause the sensor to output a positive pressure reading during this period. If the user is in a vehicle or home with air conditioning or heat running, that could also cause the sensor to output a positive pressure reading during this period. These are just examples of system noise and/or environmental conditions that could cause the sensor 18 to output a non-zero signal during the pause in breathing.

In this disclosure, the controller 20 stores the output of the sensor 18 during the pause in breathing. In particular, the controller 20 averages the values (i.e., the output of the sensor 18) of each of the predetermined amount of pressure readings taken during the pause in the breathing cycle. So, for example, the controller 20, beginning at point 90, will take 16 pressure readings and average those pressure readings. The average value is stored. Further, before the next breathing cycle, the baseline value is set by averaging the average pressure readings taken and stored during the pauses of a predetermined amount of preceding breathing cycles. In other words, the average value stored in FIG. 11 is averaged with values that were taken and stored during the preceding pauses in the breathing cycle. In an example, the baseline value used for a given breathing cycle is based on a running average of the average pressure readings taken during pauses of the 20 preceding breathing cycles. By basing the baseline value on a running average, changes in environmental conditions and system noise are properly accounted for without the user noticing any dramatic, abrupt changes to the operation of the POC.

In one particular aspect of this disclosure, the pressure sensor 18 is a differential pressure sensor with a first port in fluid communication with the tube 24 and a second port exposed to the internal conditions of the oxygen supply 14, and namely exposed inside the outer housing (or inside the "box") of the oxygen supply 14. As such, this disclosure does not use a pressure sensor 18 which includes a port exposed to the outside environment (i.e., environmental conditions outside the "box"). The control strategy discussed above is effective in eliminating the influence of system noise, even that which occurs inside the box, during use.

It should be understood that terms such as "generally," "substantially," and "about" are not intended to be boundaryless terms, and should be interpreted consistent with the way one skilled in the art would interpret those terms. Further, various directional terms, such as "superior," "inferior," "distal," "proximal," etc., have been used herein and labeled in some figures for ease of reference. These directional terms are used with reference to the normal operational Although the different examples have the specific components shown in the illustrations, embodiments of this disclosure are not limited to those particular combinations. It is possible to use some of the components or features from one of the examples in combination with features or components from another one of the examples. In addition, the various figures accompanying this disclosure are not necessarily to scale, and some features may be exaggerated or minimized to show certain details of a particular component or arrangement.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A nasal fitting for an oxygen delivery system, comprising:
a main body, the main body including a proximal surface faced in a proximal direction towards a patient and configured to rest against a philtrum of the patient;
a first prong and a second prong each projecting laterally from opposed lateral sides of the main body, wherein the first prong includes a first internal passageway and the second prong includes a second internal passageway;
a discharge port defining an opening in a superior surface of the main body, wherein the discharge port is in fluid communication with the first and second internal passageways and configured to be situated inferior to a nose of the patient;
an inclined wall surrounding at least a portion of the opening of the discharge port and slanting in an inferior direction from first and second curves of an apex towards the opening of the discharge port, wherein the apex is superior to the opening of the discharge port, and wherein the first curve of the apex at least partially surrounds a first lateral side of the discharge port and the second curve of the apex at least partially surrounds a second lateral side of the discharge port; and
wherein the fitting does not include nostril prongs, and no portion of the fitting is configured to project from the superior surface towards the nose of the patient.

2. The nasal fitting of claim 1, wherein the apex defines a superior-most portion of the nasal fitting and wherein the first and second curves of the apex lie in a common plane.

3. The nasal fitting of claim 2, wherein the plane is inclined at an angle relative to the proximal direction.

4. The nasal fitting of claim 2, wherein the inclined wall is inclined at an acute angle relative to the plane.

5. A nasal fitting for an oxygen delivery system, comprising:
a main body, the main body including a proximal surface faced in a proximal direction towards a patient and configured to rest against a philtrum of the patient;
a first prong and a second prong each projecting laterally from opposed lateral sides of the main body, wherein the first prong includes a first internal passageway and the second prong includes a second internal passageway;
a discharge port defining an opening in a superior surface of the main body, wherein the discharge port is in fluid communication with the first and second internal passageways and configured to be situated inferior to a nose of the patient;
an inclined wall surrounding at least a portion of the opening of the discharge port;
wherein the fitting does not include nostril prongs, and no portion of the fitting is configured to project from the superior surface towards the nose of the patient; and
wherein the discharge port includes a divider which divides the opening of the discharge port into a first section and a second section, the divider including a central portion providing a superior-most portion of the divider, a first wall slanting in an inferior direction from the central portion towards the first section, and a second wall slanting in the inferior direction from the central portion towards the second section.

6. The nasal fitting of claim 1, further comprising a cavity in the main body, the cavity in fluid communication with the first and second internal passageways of the first and second prongs and in fluid communication with the opening of the discharge port.

7. The nasal fitting of claim 6, wherein the main cavity includes a bottom wall located in an inferior direction relative to the opening of the discharge port, wherein the bottom wall is convex when viewed from a superior location.

8. The nasal fitting of claim 1, wherein the inclined wall includes a notch at a distal-most portion of the inclined wall.

9. The nasal fitting of claim 1, wherein the proximal surface is concave when viewed from the proximal direction.

10. The nasal fitting of claim 9, wherein the proximal surface exhibits a contour following a first constant radius $R_1$ relative to a reference point, the reference point on a centerline of the nasal fitting and spaced apart from the main body in the proximal direction.

11. The nasal fitting of claim 10, wherein the first and second prongs each include a proximal surface that exhibits a contour following a second constant radius $R_2$ relative to the reference point, wherein the second constant radius $R_2$ is larger than the first constant radius $R_1$.

12. The nasal fitting of claim 1, wherein the first and second prongs each include a superior surface which is concave when viewed from a superior location.

13. The nasal fitting of claim 1, wherein the first prong and the second prong each include an inlet port in fluid communication with the first and second internal passageways, respectively, the inlet ports each configured to receive a portion of an oxygen delivery tube.

14. The nasal fitting of claim 13, wherein the inlet ports of the first and second prong are located in an inferior direction relative to the discharge port.

15. The nasal fitting of claim 1, wherein the fitting is provided by an integrally molded piece of plastic.

16. The nasal fitting of claim 1, wherein the fitting is symmetrical about a plane containing a centerline of the fitting and extending in a superior and inferior direction.

17. The nasal fitting of claim 1, wherein the main body includes a length L extending between the opposed lateral sides of the main body and includes a height H between the superior surface and an inferior surface of the main body, and a ratio of the length L to the height H of the main body is about 2.2:1.

18. An oxygen delivery system, comprising:
an oxygen supply;
a tube configured to connect to the oxygen supply;
a fitting that does not include nostril prongs, the fitting including:
a main body, the main body including a proximal surface faced in a proximal direction towards a patient and configured to rest against a philtrum of the patient,
a first prong and a second prong each projecting laterally from opposed lateral sides of the main body, wherein the first prong and the second prong each include an internal passageway and an inlet port in communication with the internal passageway, each inlet port configured to receive a portion of the tube,
a discharge port defining an opening in a superior surface of the main body, wherein the discharge port is in fluid communication with the internal passageways of the first and second prongs and configured to be situated inferior to a nose of the patient, and an inclined wall surrounding at least a portion of the opening of the discharge port and slanting in an inferior direction from first and second curves of an apex towards the opening of the discharge port, wherein the apex is superior to the opening of the discharge port, and wherein the first curve of the apex at least partially surrounds a first lateral side of the discharge port and the second curve of the apex at least partially surrounds a second lateral side of the discharge port.

19. The oxygen delivery system of claim 18, further comprising:

a pressure sensor configured to generate signals indicative of pressure in the tube; and a controller configured to:

read the signals from the pressure sensor, detect a plurality of pauses in a breathing cycle of the patient, take a plurality of pressure readings during each pause in the breathing cycle, store an average pressure reading of the plurality of pressure readings for each pause, determine a baseline value based on a running average of the average pressure readings for the plurality of pauses, the baseline value continuously updating based on the average pressure reading of each pause; and detect an inhale of the patient when a difference between a pressure reading and the baseline value is less than or equal to an inhale threshold.

20. The nasal fitting of claim 2, wherein:

the first prong and the second prong each include an inlet port in fluid communication with the first and second internal passageways, respectively, the inlet ports each configured to receive a portion of an oxygen delivery tube; and the inlet ports are each located inferior to the plane.

* * * * *